United States Patent
Hikosaka et al.

(10) Patent No.: US 7,871,548 B2
(45) Date of Patent: Jan. 18, 2011

(54) PROCESS FOR PRODUCING POLYMER ORIENTED CRYSTAL, POLYMER ORIENTED CRYSTAL PRODUCED BY SAID PRODUCTION PROCESS, AND METHOD FOR DETERMINING CRITICAL ELONGATION STRAIN RATE OF POLYMER MELT

(75) Inventors: Masamichi Hikosaka, Higashihiroshima (JP); Kaori Watanabe, Higashihiroshima (JP)

(73) Assignee: National University of Corporation Hiroshima University, Higashihiroshima-shi (JP)

( * ) Notice: Subject to any disclaimer, the term of this patent is extended or adjusted under 35 U.S.C. 154(b) by 176 days.

(21) Appl. No.: 12/065,197

(22) PCT Filed: Aug. 31, 2006

(86) PCT No.: PCT/JP2006/317248

§ 371 (c)(1),
(2), (4) Date: Feb. 28, 2008

(87) PCT Pub. No.: WO2007/026832

PCT Pub. Date: Mar. 8, 2007

(65) Prior Publication Data
US 2009/0249883 A1    Oct. 8, 2009

(30) Foreign Application Priority Data
Sep. 2, 2005    (JP)    ............... 2005-255653

(51) Int. Cl.
*G01B 21/32*    (2006.01)
*G01N 3/00*    (2006.01)
*B29C 47/92*    (2006.01)

(52) U.S. Cl. ............ 264/40.7; 264/40.1; 73/762; 73/760; 73/818

(58) Field of Classification Search ............... 73/760, 73/762, 818; 264/180, 40.1, 40.7
See application file for complete search history.

(56) References Cited

FOREIGN PATENT DOCUMENTS

JP    60 89333    5/1985

(Continued)

OTHER PUBLICATIONS

Somani et al. "Shear-Induced Molecular Orientation and Crystallization in Isotactic Polypropylene: Effects of the Deformation Rate and Strain" Macromolecules 2005, vol. 38. pp. 1244-1255. Available Jan. 22, 2005. Accessed online Dec. 8, 2009. <http://pubs.acs.org/doi/pdf/10.1021/ma048285d>.*

(Continued)

*Primary Examiner*—Lisa M Caputo
*Assistant Examiner*—Jonathan Dunlap
(74) *Attorney, Agent, or Firm*—Oblon, Spivak, McClelland, Maier & Neustadt, L.L.P.

(57) ABSTRACT

A method and means for determining a critical elongation strain rate of a polymer melt, which make it possible to subject a polymer melt to elongation to prepare a bulk oriented melt, are established, and a process for producing bulk polymer oriented crystals and polymer oriented crystals are provided. In the critical elongation strain rate determination process or critical elongation strain rate determining method, a polymer melt (3) in a disc shape having a radius $x_0$ and a thickness of $\Delta z_0$ is held between transparent plates (an upper transparent plate (1) and a lower transparent plate (2)). The polymer melt (3) is cooled to a supercooled state and is press in a thickness direction at a constant rate v by using the transparent plates. The critical point radius $x^*$, at which the polymer melt (3) is turned to an oriented crystal, is measured, and the critical elongation strain rate $\epsilon$ is calculated by equation $\epsilon^* = ax^{*3}$ wherein $\alpha = v/(2\Delta z_0 x_0^3)$.

9 Claims, 8 Drawing Sheets

FOREIGN PATENT DOCUMENTS

| | | |
|---|---|---|
| JP | 61 193836 | 8/1986 |
| JP | 7 243120 | 9/1995 |
| JP | 9 316283 | 12/1997 |
| JP | 2000 218750 | 8/2000 |
| JP | 2003 41074 | 2/2003 |

OTHER PUBLICATIONS

Buerger et al. "Crystallization of sheared polymer melts: poly(ethylene oxide) fractions" Polymer Bulletin, vol. 22, Nos. 5-6, pp. 593-598. Available Dec. 1989. Accessed online Dec. 8, 2009. <http://www.springerlink.com/content/j061134408337664/fulltext.pdf>.*

Kumaraswamy et al. "Shear-Enchanced Crystallization in Isotactic Polypropylene. 1. Correspondence between in Situ Rheo-Optics and ex Situ Structure Determination" Macromolecules 1999, vol. 32. pp. 7537-7547. Available Oct. 7, 1999. Accessed online Dec. 8, 2009 <http://pubs.acs.org/doi/pdf/10.1021/ma990772j>.*

Kaori Watanabe, et al., "Mechanism of Acceleration of Growth Rate under Shear Flow-Universal role of "oriented melt" on crystalline surface", Hiroshima University VBL, Polymer Preprints, vol. 54, No. 1, 2C02, 2005, 4 pages (with full English translation).

Mitsuyoshi Fujiyama, "Structure of skin layer of injection-molded polypropylene", Kobunshi Ronbunshu, vol. 32, No. 7, Jul. 1975, 29 pages (with full English translation).

A. Keller at al., "Oriented Crystallization in Polymers", J. Macromol. Sci. (Phys.), B1(1), 1967, pp. 41-91.

Shinichi Yamazaki, et al., "Formation mechanism of shish in the oriented melt (I)—bundle nucleus becomes to shish", Science Direct, Elsevier, Polymer, 46, 2005, pp. 1675-1684.

Shinichi Yamazaki, et al., "Formation mechanism of shish in the oriented melt (II)—two different growth mechanisms along and perpendicular to the flow direction", Science Direct, Elsevier, Polymer, 46, 2005, pp. 1685-1692.

Bernhard Wunderlich, et al., "Polyethylene Crystallized from the Melt under Elevated Pressure", Journal of Polymer Science part A, vol. 2, 1964, pp. 3697-3706.

Masamichi Hikosaka, "Unified theory of nucleation of folded-chain crystals and extended-chain crystals of linear-chain polymers", Polymer, vol. 28, Jul. 1987, pp. 1257-1264.

* cited by examiner

PROCESS FOR PRODUCING POLYMER ORIENTED CRYSTAL, POLYMER ORIENTED CRYSTAL PRODUCED BY SAID PRODUCTION PROCESS, AND METHOD FOR DETERMINING CRITICAL ELONGATION STRAIN RATE OF POLYMER MELT

TECHNICAL FIELD

The present invention relates to a method for producing a polymer oriented crystal (that is, polymer oriented crystals) excellent in various properties such as mechanical strength, heat tolerance, and transparency, and polymer oriented crystals produced by the same method. Further, the present invention relates to a method for determining a critical elongation strain rate of a polymer melt.

BACKGROUND ART

So-called "general-purpose plastic" such as polyethylene (hereinafter, referred to as "PE") polypropylene (hereinafter, referred to as "PP"), polystyrene (hereinafter, referred to as "PS"), polyvinyl chloride (hereinafter referred to as "PVC") are very popular material as various daily-use products (such as bag, various wrapping, various container, sheets, etc.) industrial parts of automobiles, electronic products, daily-use products, general merchandise, and the like, not only because they are very low in price (100 yen or less per kg) but also because they can be easily molded, and are light in weight (one severalth of these of metal and ceramics).

However, the general-purpose plastics are disadvantages in terms of mechanical strength and heat tolerance. Because of this, the application of general-purpose plastics is limited today, because the general-purpose plastics cannot satisfy the property requirements for various industrial products such as mechanical products such as automobiles, electric, electronic, and information products. For example, PE has a softening temperature of generally about 90° C. PP, which is relatively heat tolerant, is softened at about 130° C. in general. Moreover, PP is insufficient in transparency compared with polycarbonate (hereinafter, referred to as "PC"), and polyethylene terephthalate (hereinafter, referred to as "PET"). The insufficient transparency prevents PP from being used as optical products, bottle, and transparent container.

On the other hand, so-called "engineering plastics" such as PET, PC, fluoroplastics (Teflon (Registered Trademark) etc.), nylon, polymethylpentene, polyoxymethylene, acrylic resin, are excellent in mechanical strength, heat tolerance, transparency, etc. The engineering plastics, which are not softened at a temperature of 150° C. in general, are used as various industrial product materials and optical materials, which require high property, for automobiles, mechanical products and electric products. On the other hand, the engineering plastics are significantly disadvantageous. For example, they are very expensive (several hundred yen/kg to several thousands yen/kg). Further, the engineering plastics are very environmental unfriendly because monomer recycle thereof is difficult or impossible.

Therefore, large improvement of the general-purpose plastics in material properties such as mechanical strength, heat tolerance, and transparency, etc. would allow the general-purpose plastics to replace the engineering plastics, and further the metal materials. This will significantly reduce the cost of various industrial products and daily-use products, which are made of polymer or metal. Further, this will give light weight to the various industrial products and daily-use products, thereby attaining great reduction in energy consumption and great improvement in handling. For example, PET is used in bottles for drinks such as soft drinks. If PET is replaced with PP, the cost of the bottle can be reduced significantly. Moreover, the monomer recycle of PET is possible but not easy. Thus, used PET bottles are cuts in pieces and reused once or twice for low-quality purposes such as cloths fibers, films, etc., and then discarded. On the other hand, PP is easy to perform monomer recycle and can be completely recycled. The use of PP can reduce consumption of fossil fuel and $CO_2$ production.

In order to improve the general-purpose plastics in properties such as mechanical strength, heat tolerance, transparency, etc. to replace the engineering plastics and metals with the general-purpose plastics, it is necessary to improve PP and PE in crystal ratio (crystallinity) significantly, and preferably to produce "crystal" which is a pure crystal contain almost no amorphous PP or PE. Especially, PP is higher in mechanical strength and heat tolerance than PE. Thus, advantage of PP is highly expected. Annual production of PP is increased steadily by several % each year.

One method known to improve the crystallinity of polymer is to cool the polymer melt at a slow rate. This method, however, cannot attain sufficient improvement in the crystallinity at all. Further, this method leads to significant deterioration in productivity of the product and low mechanical strength due to huge crystal particle size. Another known method is to cool the melted polymer solution under high pressure in order to increase the crystallinity. This method, however, need pressuring the polymer melt at several hundreds atm or greater. Thus, this method is only experimentally possible, but not feasible in industrial production due to complicate production apparatus design and high production cost. Thus, this method is difficult to adopt practically. One another known method to improve the polymer crystallinity is to add a nucleating agent in the polymer melt. However, this method currently so disadvantageous that it cannot avoid (a) contamination with the nucleating agent as impurity (b) increase in cost due to higher cost of the nucleating agent than resin. In conclusion, there is no method to improve the crystallinity of the polymer in the general-purpose plastic and to produce the "crystal" of the polymer at this moment.

Incidentally, many study showed that a polymer melt (isotropic melt) in which molecular chains take random conformation (so called "random coil") is crystallized with a mixture of shish crystal form and kebab crystal form when crystallized under shear flow (see Non-Patent Citation 1). The shish crystal form is fiber-like crystal of several μm in thickness and is formed along the flow. The kebab crystal form is a lamination of thin-film crystal and amorphous skewered through the shish crystal form. This form is referred to as "shish-kebab" like Japanese Yakitori's stick and meat.

In the production of shish-kebab form, only the shish form is created locally in an initial period. The shish form has Elongated Chain Crystal (ECC) structure in which straightly-elongated molecular chains are crystallized (see Non-Patent Citation 5). On the other hand, the crystal portion of the kebab form has a Folded Chain Crystal (FCC) structure in which the molecular chains are folded at a surface of the thin-film crystal. How the shish-kebab form is produced has not been explained in terms of molecular theory, because it has not been studies kinetically. The FCC is a thin-film crystal (called lamellar crystal) which is most widely seen among polymer crystals. Moreover, it is widely known that injection molding forms a "skin" (which is a thin crystalline film of several hundred μm thickness) on surface, and a "core" inside. The core is a "lamination structure (lamination lamellar structure)" in which a folded chain crystal and amorphous are laminated. (see Non-Patent Citation 6). The skin formed from shish-kebab form but the shish is formed only sparsely. Production mechanism of the skin structure has been totally unknown in the lack of kinetic study thereon.

The inventors of the present inventions are pioneers to study the production mechanism of the shish form kinetically, and found the mechanism of the local formation of the shish form in the melt: at a boundary with heterogeneity, some molecular chains in the melt attain liquid crystal orientation because the molecular chains are elongated due to "topological interaction" with the boundary, and the melt become "Oriented melt". (See Non-Patent Citations 2 and 3 for example.) Here, the topological interaction is an effect that string-like polymer chains pull each other because they are entangled. The topological interaction is well-known as a characteristic interaction among polymers. The inventors of the present invention are first to report the topological crystallization mechanism theory of polymers, explaining how the ECC and FCC are formed. This theory is called "sliding diffusion theory" and recognized worldwide. (See Non-Patent Citation 7.)

Moreover, the inventors of the present invention reports the general theory of the mechanism how the crystallization under low shear rate elongates the molecular chains to form the oriented melt thereby to speed up nucleation and growth speed. (See Non-Patent Citation 4.)

Based on these, it is expected that the polymer crystallization will be facilitated and high crystallinity can be achieved if the whole polymer melt become oriented melt. Here, the polymer melt become oriented melt wholly is referred to as bulk oriented melt. Further it is expected that if the bulk oriented melt can be crystallized with the orientation, "crystal" in which majority (preferably 50% or more) of the polymer molecular chains are oriented can be produced. (The crystal is referred to as bulk "polymer oriented crystals".) In this case, the nucleation is significantly facilitated and a vast number of nuclei is created between molecular chains without adding nucleating agent thereto. This eliminates the need of the addition of the impurity and allows the crystal size to be in nano meter order. It is expected that this leads to polymers with high transparency and dramatic improvement in mechanical strength and heat tolerance.

[Non-Patent Citation 1]
A. Keller, M. J. Machin, J. Macromol. Sci., Phys., B2, 501 (1968)

[Non-Patent Citation 2]
S. Yamazaki, M. Hikosaka et al, Polymer, 46, 2005, 1675-1684.

[Non-Patent Citation 3]
S. Yamazaki, M. Hikosaka et al, Polymer, 46, 2005, 1685-1692.

[Non-Patent Citation 4]
Watanabe, et al., 2005 Annual Meeting of the Society of Polymer Science, Polymer Preprints, Japan, 54(1), 626

[Non-Patent Citation 5]
B. Wunderlich, T. Arakawa, J. Polym. Sci., 2, 3697-3706 (1964)

[Non-Patent Citation 4]
Terumi FUJIYAMA, "Structure of Skin Layer of Extruded Polypropylene", Polymer Preprints, 32(7), PP 411-417 (1975)

[Non-Patent Citation 7]
M. Hikosaka, Polymer 1987 28 1257-1264

As described above, it is theoretically expected that bulk polymer oriented crystals can be obtained by preparing a bulk oriented melt from a polymer melt and then crystallizing the oriented melt by cooling. Non-Patent Citations 2 and 3 discloses critical strain rate ("critical shear strain rate $\gamma^*$") at which oriented melt can be produced partly under shear flow. However, bulk oriented melt cannot be produced by applying shear to the polymer melt at strain rate equal to or greater than the critical shear strain rate, which produces the oriented melt only partly in the vicinity of the boundary with the heterogeneity. (In this case, the strain rate is a critical strain rate under shear deformation, that is, under shear flow. Meanwhile, later-described $\epsilon^*$ is a critical strain rate under elongation flow.) Here, $\gamma^*$=about $0.3 s^{-1}$, which is smaller by one digit than the later described $\epsilon^*$=about several ten $s^{-1}$. Thus, the bulk polymer oriented crystals cannot be obtained even if the information based on the critical shear strain rate recited in the Non-Patent Citations is used. That is, no method has not been established, which determines the critical strain rate (critical elongation strain rate), which can straighten the polymer in the polymer melt in the bulk oriented melt. Moreover, even if the critical elongation strain rate can be determined, the critical elongation strain rate varies depending on type of the polymer, polymerization rate of the polymer, and molecular weight distribution in the polymer, and entangling density, melting temperature, and the like. Thus, the critical elongation strain rate should be determined for each polymer. Thus, at this moment, the bulk polymer oriented crystals cannot be produced by applying the technologies described above.

An object of the present invention is to establish method and means for determining the critical elongation strain rate in the polymer melt, which method and means allows preparation of the bulk oriented melt by straitening the molecular chains in the polymer melt. Further, an object of the present invention is to improve the crystallinity of polymers by this method and means. Finally, an object of the present invention is to provide a method for producing the bulk polymer oriented crystals and bulk polymer oriented crystals produced by the same method.

DISCLOSURE OF INVENTION

As a result of diligent studies to solve the aforementioned problems, the inventors of the present invention uniquely developed a Compression-type crystallization apparatus, which can determine a critical elongation strain rate of a polymer melt by a single test, which has been difficult to determine. The present invention is accomplished by finding means for determining the critical elongation strain rate by using the Compression-type crystallization apparatus.

A method according to the present invention is a method for producing polymer oriented crystals, the method comprising: preparing oriented melt by subjecting a polymer melt to elongation at a strain rate equal to or greater than a critical elongation strain rate so as to put the polymer melt in a oriented melt state; and rapidly cooling the polymer oriented melt to crystallize it while keeping the oriented melt state.

Moreover, the method according to the present invention may comprise determining the critical elongation strain rate of the polymer melt.

The step of determining may be a step including: sandwiching the polymer melt with transparent boards, the polymer melt having a disc shape with a radius of $x_0$ and a thickness of $\Delta z_0$; supercooling the polymer melt; pressing the polymer melt at a constant rate v in a thickness direction by using the transparent boards; measuring a critical point radius $x^*$ at which oriented crystals are formed from the polymer melt; and calculating the critical elongation strain rate from:

$$\epsilon^* = \alpha x^{*3},$$

where $\alpha = v/(2 x_0^3 \Delta z_0)$.

The step of determining may be a step including: sandwiching the polymer melt with transparent boards, the polymer melt having a rectangular shape with a center distance of $x'_0$, a thickness of $\Delta z_0$, and a constant width; supercooling the polymer melt; pressing the polymer melt at a constant rate v in a thickness direction by using the transparent boards; measuring a critical point center distance $x'^*$ at which oriented crystals are formed from the polymer melt; and calculating the critical elongation strain rate from:

$$\epsilon^* = \alpha x'^{*2},$$

where $\alpha = v/(2 x'_0{}^2 \Delta z_0)$.

According to these methods, the polymer melt is turned to a bulk oriented melt by subjecting the polymer melt to elongation at a strain rate equal to or greater than the critical elongation strain rate, and then the polymer melt in the oriented melt state is cooled to be crystallized. In this way, a bulk oriented crystal of polymer (which may be called "polymer oriented crystals") can be obtained.

The method according to the present invention may be arranged preferably such that the polymer melt is a polypropylene melt. The method according to the present invention may be arranged more preferably such that the polymer melt is an isotactic polypropylene melt.

According to the method, it is possible to obtain polymer oriented crystals of polypropylene. The polymer oriented crystals of polypropylene are improved in heat tolerance, mechanical strength, etc., and is highly transparent due to its crystal molecules of nano meter order. Here, what is meant by the mechanical strength is overall strength such as breaking strength, rigidity, toughness, etc. Moreover, it is more preferable that the polypropylene is isotactic polypropylene in which methyl groups are oriented in one direction, because this further improves crystallinity, thereby improving the properties. This makes it possible to use polypropylene in various industrial parts of automobiles, electronic products, and the other products, to which polypropylene has not been applicable conventionally due to its poor mechanical strength, heat tolerance, etc. This can make a significant reduction in the cost of the industrial parts, etc. Moreover, as described above, monomer recycle of PP is easy. Thus, the use of PP lowers the consumption of fossil fuels thereby contribution to $CO_2$ reduction, which is worked on worldwide.

Meanwhile, polymer oriented crystals according to the present invention are polymer oriented crystals produced by any method mentioned above. The polymer oriented crystals are significantly high in crystallinity compared with conventional polymers, and has a very small crystal size of nano meter order. Therefore, the polymer oriented crystals are improved in properties such as heat tolerance, mechanical strength, toughness, transparency, etc.

A method according to the present invention for determining a critical elongation strain rate of a polymer melt comprises: sandwiching the polymer melt with transparent boards, the polymer melt having a disc shape with a radius of $x_0$ and a thickness of $\Delta z_0$; supercooling the polymer melt; pressing the polymer melt at a constant rate v in a thickness direction by using the transparent boards; measuring a critical point radius $x^*$ at which oriented crystals are formed from the polymer melt; and calculating the critical elongation strain rate $\epsilon^*$ from:

$$\epsilon^* = \alpha x^{*3},$$

where $\alpha = v/(2 x_0{}^3 \Delta z_0)$.

A method according to the present invention for determining a critical elongation strain rate of a polymer melt comprises: sandwiching the polymer melt with transparent boards, the polymer melt having a rectangular shape with a center distance of $x'_0$, a thickness of $\Delta z_0$, and a constant width; supercooling the polymer melt; pressing the polymer melt at a constant rate v in a thickness direction by using the transparent boards; measuring a critical point center distance $x'^*$ at which oriented crystals are formed from the polymer melt; and calculating the critical elongation strain rate $\epsilon^*$ from:

$$\epsilon^* = \alpha x'^{*2},$$

where $\alpha = v/(2 x'_0{}^2 \Delta z_0)$.

According to the method, it is possible to determine the critical elongation strain rate of the polymer melt by testing the polymer sample one with ease, even though the critical elongation strain rate has not been determinable conventionally. By applying the critical elongation strain rate of the polymer to the method according to the present invention for producing the polymer oriented crystals, it becomes possible to produce polymer oriented crystals that have not been obtainable conventionally.

As described above, the present invention makes it possible to produce bulk polymer oriented crystals, thereby making it possible to use a general-purpose plastic in replacement of engineering plastics. This leads to great reduction in the cost of various industrial products made of polymer. Moreover, the present invention can give the polymer a strength equivalent to that of metals. Thus, the present invention makes it possible to use a general-purpose plastic in replacement of metals. The use of the general-purpose plastic in replacement of metals reduces the weight of conveyance apparatus to one severalth, because the specific gravity of the general-purpose plastic is one eighth of the metal. This reduces fuel consumption, thereby making a great contribution to energy saving.

For a fuller understanding of the nature and advantages of the invention, reference should be made to the ensuing detailed description taken in conjunction with the accompanying drawings.

REFERENCE NUMERALS 1, 1' Upper Transparent Board
2, 2' Lower Transparent Board
3 Polymer Melt
10 Compression-type Crystallization Apparatus

BEST MODE FOR CARRYING OUT THE INVENTION

One embodiment of the present invention is described blow. It should be noted that the present invention is not limited thereto and can be modified in various ways within the scope thereof recited below.

<1. Method According to the Present Invention for Producing Polymer Oriented Crystals>

The present invention relates to a method for producing polymer oriented crystals. The method is applicable to any polymers including so-called general-purpose plastics (such as polyethylene (PE), polypropylene (PP), polystyrene (PS), and the like), so-called engineering plastics (polyethylene terephthalate (PET), nylon, fluoroplastics such as Teflon (Registered Trademark)). It is preferable to apply a general-purpose plastic to the method of present invention, because it can improve the general-purpose plastic of low cost in terms of its properties such as mechanical property, heat tolerance, transparency, etc. and allow the general-purpose plastic to replace the engineering plastic, thereby significantly reducing the cost of industrial resin parts etc. Further, PP is preferable among the general-purpose plastics, because PP is more heat-tolerable and mechanically stronger than the other general-purpose plastics. Moreover, among PP, isotactic polypropylene (hereinafter, referred to as iPP where appropriate) is especially preferable. This is because iPP has good crystallinity due to its structure in which methyl groups are oriented in one direction. Thus, it is easy to obtain the polymer oriented crystals from iPP. Moreover, the resultant polymer oriented crystals prepared from iPP can attain finer crystal molecules more easily than these prepared from general PP. Thus, the resultant polymer oriented crystals prepared from iPP have a higher transparency than these prepared from general PP.

The "bulk polymer oriented crystals" in this Description are a highly crystallized crystal having a structure in which polymer molecular chains are highly oriented and occupy majority (preferably 50% or more) of the solid portion. The polymer oriented crystals may contain amorphous in addition to the crystal. By crystallizing the polymer melt while it is in the state of oriented melt, the molecular chains contained in the oriented melt are associated with each other. This leads to nucleation and crystal growth without assistance of heterogeneity. Thereby, the polymer oriented crystals are produced.

Generally, in the melt of polymer (referred to as "polymer melt"), the polymer molecular chains are present with random and isotropic form (for example, in a random coil form). Such a polymer melt is referred to as "isotropic melt". Application of external force such as shearing force, elongation, etc. to the isotropic melt straightens the polymer molecular chains. The straightened polymer molecular chains go back to the random state by entropic relaxation thermodynamically. If the external force is applied at a strain rate equal to or greater than a certain level, the application overrules the entropic relaxation that causes the molecular chains to return to the random state. As a result, a melt with high orientation of the molecular chains is obtained (which is called as oriented melt). The strain rate at which the polymer isotropic solution can be turned to the oriented melt is called "critical strain rate". Especially, the critical strain rate at which the polymer melt is turned to the bulk oriented melt by straightening the molecular chains is called "critical elongation strain rate".

Therefore, the production of the bulk polymer oriented crystals need subjecting the polymer melt to elongation at a strain rate equal to or greater than the critical elongation strain rate.

However, a method and means for determining the critical elongation strain rate has not been established. In the following, a "step of determining the critical elongation strain rate" is explained, which can determine the critical elongation strain rate of the polymer melt. The method of the present invention for producing the polymer oriented crystals preferably may or may not comprises this step.

<1-1: Step of Determining the Critical Elongation Strain Rate>

The inventors of the present invention developed a compression-type crystallization apparatus by themselves, which can determine the critical elongation strain rate. This crystallization apparatus makes it possible to directly observe the elongation crystallization of the polymer melt by using an optical microscope. A structure of the crystallization apparatus is explained referring to the schematic view of FIG. 1. A crystallization apparatus 10 comprises a pair of transparent boards (upper transparent board 1 and a lower transparent board 2). Temperature of the transparent boards can be controlled by temperature controlling means (not illustrated). The transparent boards can be made of any material, provided that they are so transparent that a polymer sample sandwiched therebetween can be observed by the optical microscope. However, the transparent boards should sandwich the polymer melt of a high temperature. Thus, it is preferable that the transparent boards be made of a highly heat tolerant material such as glass, quartz, sapphire, or diamond. Moreover, it is preferable that the transparent boards have a flat surface.

Figure 1:
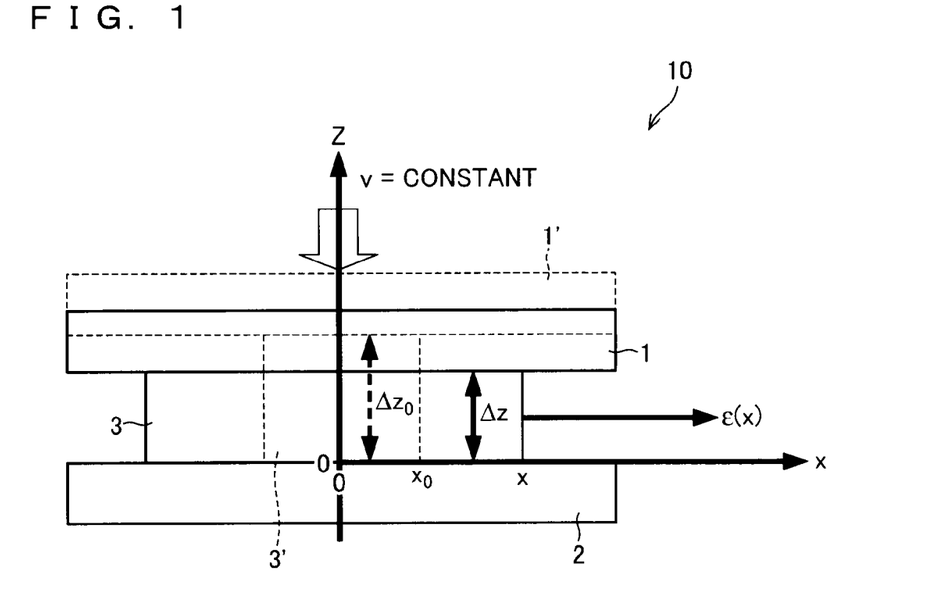
FIG. 1 is a schematic view illustrating a Compression-type crystallization apparatus for use in determination of critical elongation strain rate of a polymer melt.
Figure 8:
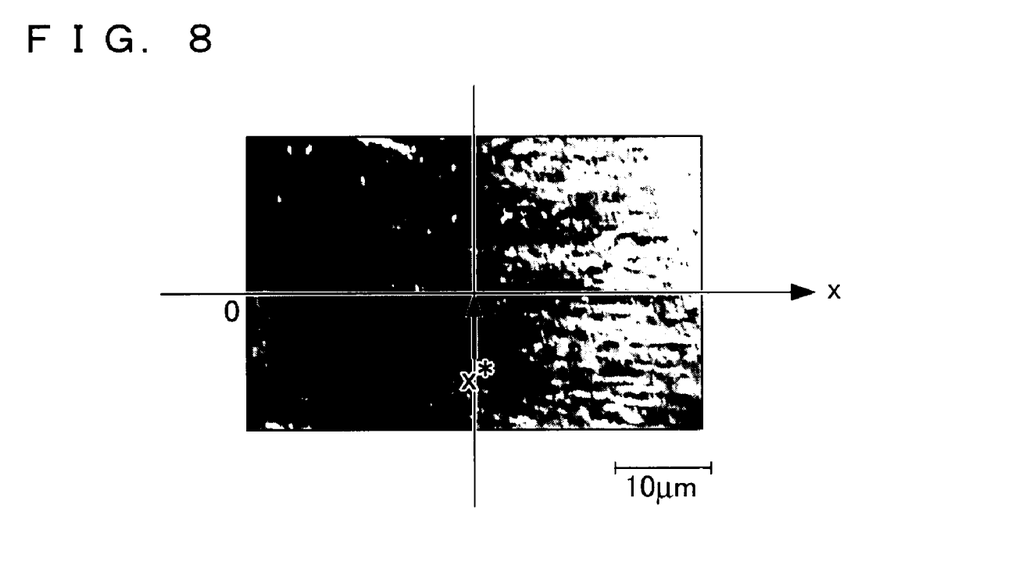
FIG. 8 is a polarization microscopic view of a sample prepared by elongation crystallization of isotactic polypropylene melt by using the compression-type crystallization apparatus in an Example.

Next, how to determine the critical elongation strain rate of the polymer melt by using the crystallization apparatus 10 is explained below. Firstly, a disc-shaped polymer melt (sample) 3' is placed on the lower transparent board 2, and then sandwiched between the upper transparent board 1 and the lower transparent board 2. Then, they are set in a polarization microscope to observe the crystallization process directly. Then, the sample is rapidly cooled (cooling rate: 20° C./min or faster) to a constant temperature (crystallization temperature) at which the polymer melt (sample) is kept supercooled (degree of supercooling $\Delta T$: 20K or greater). Then, the upper transparent board 1 is moved toward at a constant rate (rate: 3 mm/s or faster) thereby to push the polymer melt (sample) 3' in a thickness direction at a constant rate (as an alternative, the lower transparent board 2 may be moved toward the upper transparent board 1). In the polymer melt (sample) 3 thus crystallized, a portion in which the polymer melt is turned to an oriented melt and then crystallized to polymer oriented crystals is observed as a white portion with close-packed fiber-like shish via the polarization microscopic observation. On the other hand a portion in which the polymer melt is not turned to an oriented melt or oriented crystal but to isotropic melt or spherulite (which is an isotropic crystal) is observed as black or spherical white portion. FIG. 8 illustrates a polarization microscopic view in which a polymer melt (PP) was being crystallized by using the crystallization apparatus 10. The white region in FIG. 8 is a region in which bulk polymer oriented crystals have been formed form close-packed shish. The black region in FIG. 8 is a region in which isotropic melt including spherulite was present. Therefore, the boundary between the white and black region is a critical strain rate point (critical point) at which the polymer melt is turned to the polymer oriented crystals.

Referring to FIG. 1, the method for determining the critical elongation strain rate of the polymer melt is explained more specifically. The polymer melt 3' indicated by the broken line in FIG. 1 is a polymer melt before pressed down by the transparent boards (upper transparent board 1 and the lower transparent board 2). On the other hand, in FIG. 1, the polymer melt 3 indicated by the solid line is the polymer melt 3 after pressed down by the transparent boards (upper transparent board 1 and the lower transparent board 2). In FIG. 1, the upper transparent board 1' indicated by the broken line is the upper transparent board and its location before pressing the polymer sample 3 down. Moreover, the reference numeral "0" indicates a center point of the disc-shaped polymer sample.

It is put that the thickness direction is a direction from the lower transparent board 2 to the upper transparent board 1 (the z axis direction in FIG. 1), and a distance between the transparent boards between which the disc-shaped polymer melt 3 is the thickness of the disc-shaped polymer melt. Moreover, a distance from the center of the disc made of the polymer melt 3 is the radius.

Where the polymer melt 3' before pressing is (radius, thickness is $(x_0, \Delta z_0)$, and is pressed down at a constant rate v, the elongation strain rate $\epsilon(x)$ is defined as:

$$\epsilon(x)=(dx/dt)/x_0 \qquad (1).$$

Here, the polymer melt 3 is (radius, thickness)=$(x, \Delta z)$ and t is time.

From Equation (1), $v=-d\Delta z/dt \ldots (2)$, and volume conservation: $\pi x^2 \Delta z = \pi x_0^2 \Delta z_0 \ldots (3)$, $\epsilon(x)$ can be put as:

$$\epsilon(x)=\alpha x^3 \qquad (4),$$

where $\alpha=v/(2\Delta z_0 x_0^3)$.

Therefore, the elongation strain rate $\epsilon(x)$ for the disc-shaped polymer melt of radius x can be calculated from Equation (4).

Thus, by using the crystallization apparatus to find the critical point $(x^*)$ for turning the polymer melt to the oriented crystal, and entering the value of the critical point $(x^*)$ in Equation (4), the elongation strain rate $\epsilon(x^*)$ at the critical point, that is, the critical elongation strain rate $\epsilon^*$, can be determined.

This is explained below more specifically referring to FIG. 8. In FIG. 8, the reference numeral "0" corresponds to the center point "0" of the disc-shaped polymer melt in FIG. 1. As described above, the boundary between the white region and the black region indicates the critical point for turning the polymer melt to the oriented crystal. Thus, where a radius of the critical point (i.e., critical point radius) is indicated by the mark "x*" in FIG. 8. By measuring the critical point radius x*, it is possible to calculate out the critical elongation strain from Equation (4).

Figure 2:
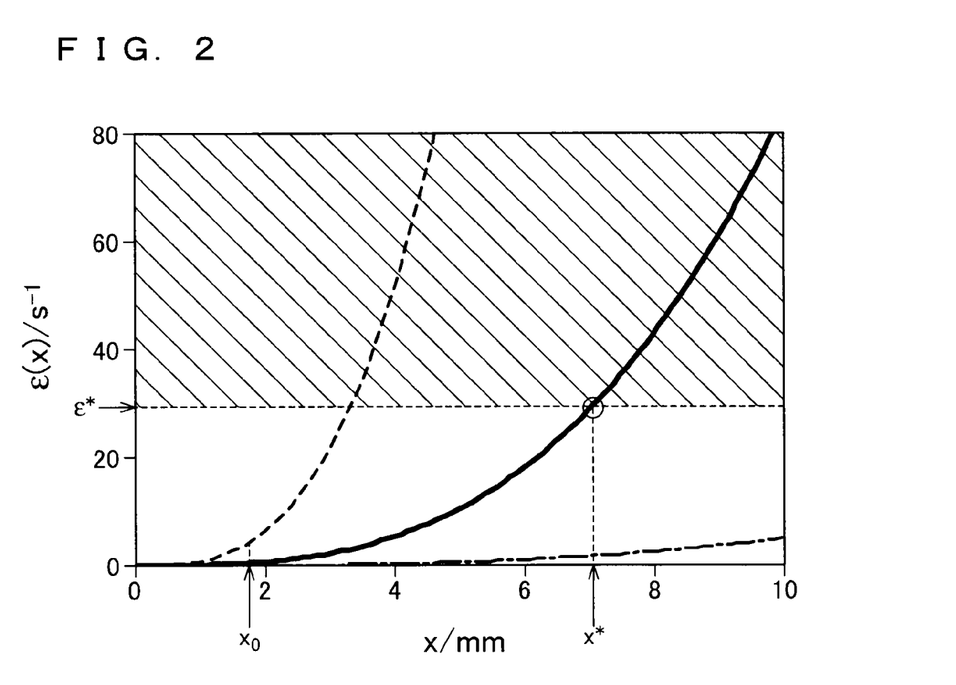
FIG. 2 is a graph plotting a radius x of a disc-shaped polymer sample against elongation strain rate $\epsilon(x)$.

In FIG. 2, curves showing the relationship between the radius x of the disc-shaped polymer melt and the elongation strain rate $\epsilon(x)$ are illustrated. The solid curve shows results of the later-described Example (v=3 mm/sec). The broken curve shows a case where v>3 mm/sec. The dashed curve shows a case where v<3 mm/sec. FIG. 2 explains that greater v results in a more significantly greater elongation strain rate $\epsilon(x)$ with the radius x. Where the elongation strain rate $\epsilon(x)$>critical elongation strain rate $\epsilon(x^*)$, the elongation of the polymer molecular chain overrules the entropic relaxation, thereby causing the oriented melt, and consequently causing the bulk polymer oriented crystals. The elongation strain rate $\epsilon$ is not dependent on v, because the elongation strain rate $\epsilon$ is a point at which the elongation effect and the entropy effect cancel out each other. Thus, with greater v, the oriented melt can be prepared more efficiently.

The use of the compression-type apparatus makes it possible to observe, by a single test, how the polymer melt is crystallized at various strain rates. Further, the finding of the critical point radius allows to determine the critical elongation strain rate of the polymer melt. Because the critical elongation strain rate can be determined by a single test, it is not necessary to conduct plural tests to observe how the polymer melt is crystallized at various strain rates respectively, and thus it is possible to eliminate influence from differences between the polymer melts and test conditions (crystallization temperatures, melting temperatures, pressing rates, etc.). Therefore, it is possible to determine the critical elongation strain rate more accurately.

Figure 3A:
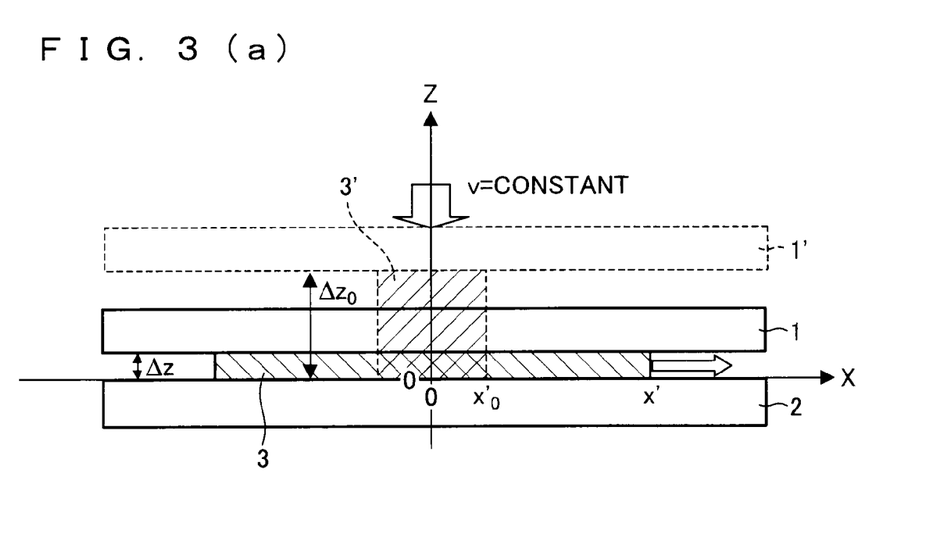
FIG. 3(a) is a side view of the Compression-type crystallization apparatus.
Figure 3B:
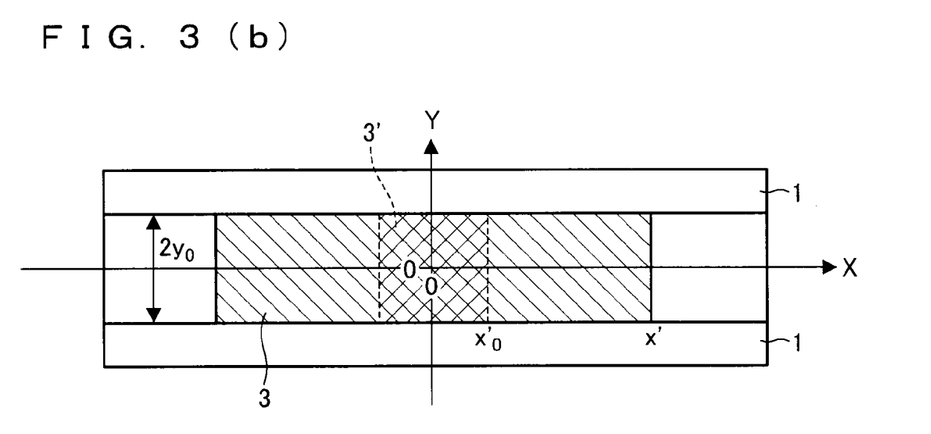
FIG. 3(b) is an upper view of the Compression-type crystallization apparatus.

It should be noted that the present invention is not limited to the Compression-type crystallization apparatus described above, in which the polymer sample in the disc shape is placed on the flat lower transparent board 2 and then tested. The critical elongation strain rate can be determined similarly with a polymer sample in a rectangular shape. One example of the Compression-type crystallization apparatus for use in determining the critical elongation strain rate with the rectangular-shaped polymer sample is illustrated in FIG. 3. FIG. 3(a) is a side view of the crystallization apparatus. FIG. 3(b) is an upper view of the crystallization apparatus. In FIG. 3, the same members are labeled in the same manner as the Compression-type crystallization apparatus shown in FIG. 1. Their explanation is omitted here. The crystallization apparatus illustrated in FIG. 3 is configured such that a lower transparent board 2 has a recess section thereon. The recess section has a rectangular shape with a constant width $(2y_0)$. Meanwhile, an upper transparent board 1 has a protrusion section thereon, which engages with the recess section. The polymer melt may be placed in the recess section and pressed down with the protrusion section.

It is put that the thickness direction is a direction from the lower transparent board 2 to the upper transparent board 1 (the z axis direction in FIG. 3), and a distance between the transparent boards between which the rectangular-shaped polymer melt is the thickness of the rectangular-shaped polymer melt. Furthermore, a direction in which the polymer melt is elongated when it is pressed down with the upper and lower transparent boards is put as a longitudinal direction (x axis direction in FIG. 3). A direction perpendicular to the longitudinal direction and the thickness direction is put as a width direction (y axis direction in FIG. 3). Moreover, a distance between a mid point and an end of a longitudinal dimension of the rectangular-shaped polymer melt is put as a center distance.

Where the polymer melt 3' before pressing is (radius, thickness is $(x'_0, \Delta z_0)$, the polymer melt 3 after pressing is (center distance, thickness)=$(x', \Delta z)$, the elongation strain rate $\epsilon(x')$ for the center distance x' attained when the polymer melt 3' is pressed at a constant rate v is defined as follows:

$$\epsilon(x')=(dx'/dt)/x'_0 \quad (1'),$$

Here, the polymer melt 3 is (center distance, thickness)=x', $\Delta z$) and t is time.
From Equation (1), $v=-d\Delta z/dt$ ... (2), and volume conservation: $x'y \Delta z = x'_0 y_0 \Delta z_0$ ... (3'), $y=y_0$, $\epsilon(x')$ can be put as:

$$\epsilon(x')=\alpha x'^2 \quad (4'),$$

where $\alpha = v/(2 x'^2_0 \Delta z_0)$.

Therefore, the elongation strain rate $\epsilon(x')$ for the rectangular-shaped polymer melt of radius x can be calculated from Equation (4').

Thus, by finding the critical point (x'*) for turning the polymer melt to the oriented crystal a described above, and entering the value of the critical point (x'*) in Equation (4'), the elongation strain rate $\epsilon(x^*)$ at the critical point, that is, the critical elongation strain rate $\epsilon^*$, can be determined.

Figure 4:
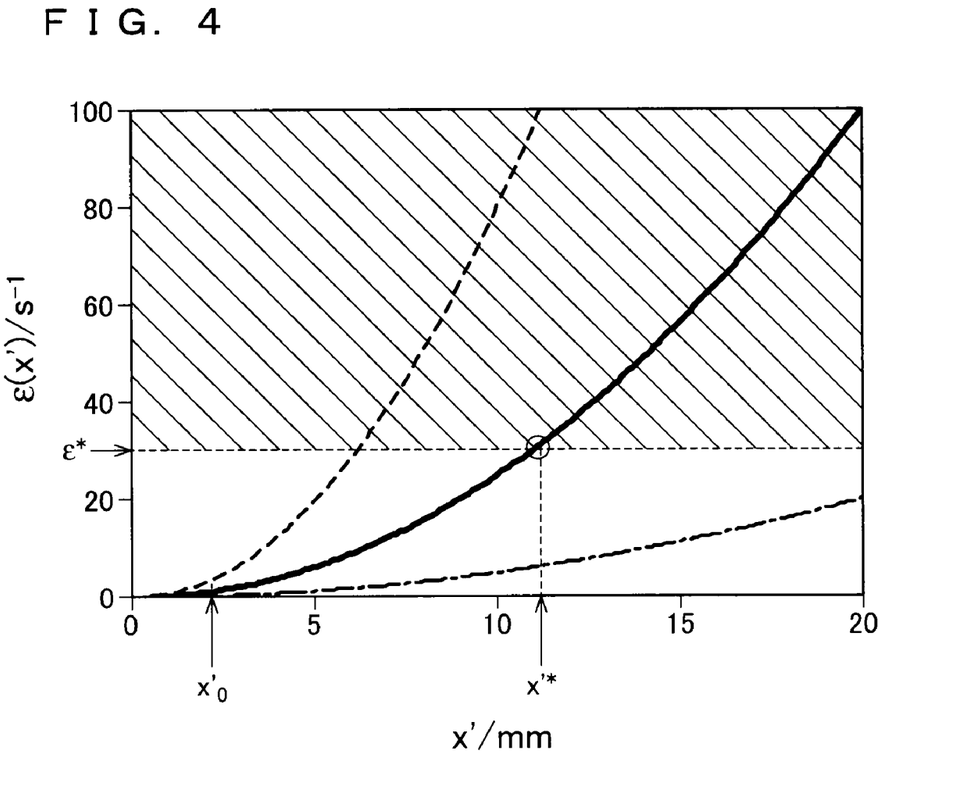
FIG. 4 is a graph plotting a center distance x' of a rectangular shaped polymer in a melt against elongation strain rate $\epsilon(x')$.

In FIG. 4, curves showing the relationship between the center distance (x') of the rectangular-shaped polymer melt and the elongation strain rate $\epsilon(x')$ are illustrated. The solid curve shows results of the later-described Example (v=3 mm/sec). The broken curve shows a case where v>3 mm/sec. The dashed curve shows a case where v<3 mm/sec. FIG. 4 explains that the greater the v, the more significantly greater the elongation strain rate $\epsilon(X')$ with the center distance x. Where the elongation strain rate $\epsilon(X')$>critical elongation strain rate $\epsilon(X'^*)$, the elongation of the polymer molecular chain overrules the entropic relaxation, thereby causing the oriented melt, and consequently causing the bulk polymer oriented crystals.

As explained above, the use of the polymer melt makes it possible to extend the polymer melt sample one-dimensionally. Thus, how the polymer is crystallized at various strain rates can be observed by using Equation (4'), thereby to easily determine the critical elongation strain rate $\epsilon^*$.

(1-2: Step of Preparing Oriented Melt)

Next, a bulk "step of preparing oriented melt" is described, which is included in the method according to the present invention for producing the polymer oriented crystals. The step of preparing oriented melt is a step for turning the polymer melt in the oriented melt state by subjecting the polymer melt at elongation at a strain rate equal to or greater than the critical elongation strain rate $\epsilon^*$ which is determined in the step of determining the critical elongation strain rate.

Figures 5A, 5B:
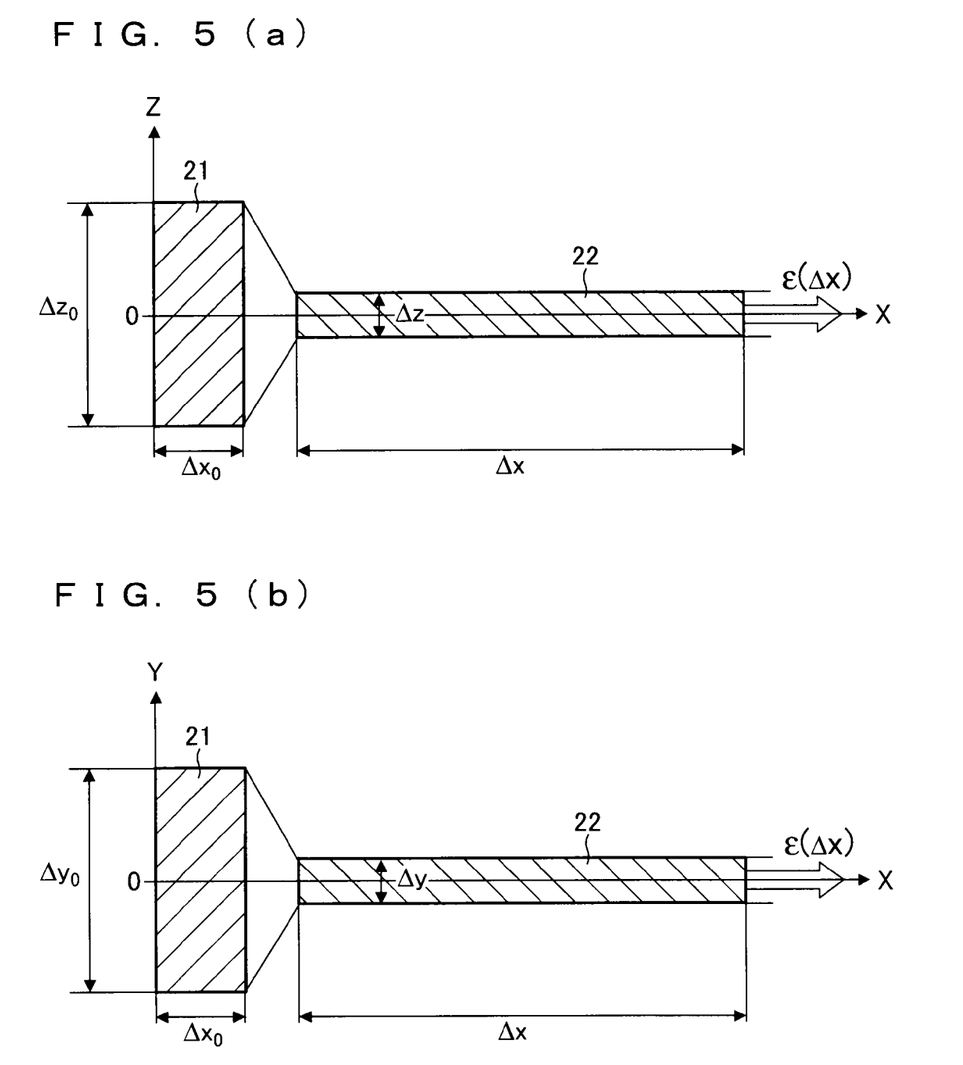
FIG. 5(a) is a side cross sectional view illustrating a die (one example) for use in a method according to the present invention for producing polymer oriented crystals.
FIG. 5(b) is a side cross sectional view illustrating a die (another example) for use in a method according to the present invention for producing polymer oriented crystals.

This step is not limited to particular elongating method, elongating means, etc., provided that the polymer melt is subjected to the elongation at strain rate equal to greater than the critical elongation strain rate. One example of the step of preparing oriented melt is explained referring to FIG. 5. It should be noted that the present invention is not limited to the present invention. FIGS. 5(a) and (b) are side cross sectional view of a die for use in sheet formation, film formation, injection molding, etc. of the polymer melt. The polymer melt can be turned to the oriented melt by elongating the molecular chain in the polymer melt at a strain rate equal to or greater than critical elongation strain rate when the polymer melt is extruded/injected via such a die, or when the polymer melt is treated with a roller or a mold thereafter.

Assume that the die illustrated in FIG. 5 is used and a board-shaped (rectangular column-shaped) polymer melt 21 with "length $\Delta x_0$, width $\Delta y_0$, and thickness $\Delta z_0$" is extruded or injected out, or deformed by using the roller or mold, is deformed to a board-shaped (rectangular column-shaped) polymer melt 22 with "length $\Delta x$, width $\Delta y$, and thickness $\Delta z$" by compression or elongation carried out for time $\Delta t$. In this case, the elongation strain rate of the polymer melt is defined as:

$$\epsilon(\beta)=(\beta-1)/\Delta t \quad (5),$$

where $\beta$ is a compression ratio, and $\beta=(\Delta y_0 \Delta z_0)/(\Delta y \Delta z)$.

The "length" is a distance between a bottom surface and an upper surface where the bottom and upper surfaces are surfaces face each other along a direction in which the polymer melt is injected. Moreover, the "width" is a length of one edge of the bottom surface or upper surface in a square shape, and the "thickness" is a length of one edge perpendicular to the edge of the "width".

Thus, the oriented melt can be prepared by performing "compression deformation" of the polymer melt with appropriately selected "width $\Delta y_0$, thickness $\Delta z_0$" of the polymer melt in the die, appropriately selected "width $\Delta y$, thickness $\Delta z$" of the polymer melt after the injection, extrusion, or deformation using the roller or molding, and appropriately selected $\Delta t$ (time required for compression deformation).

Figure 6:
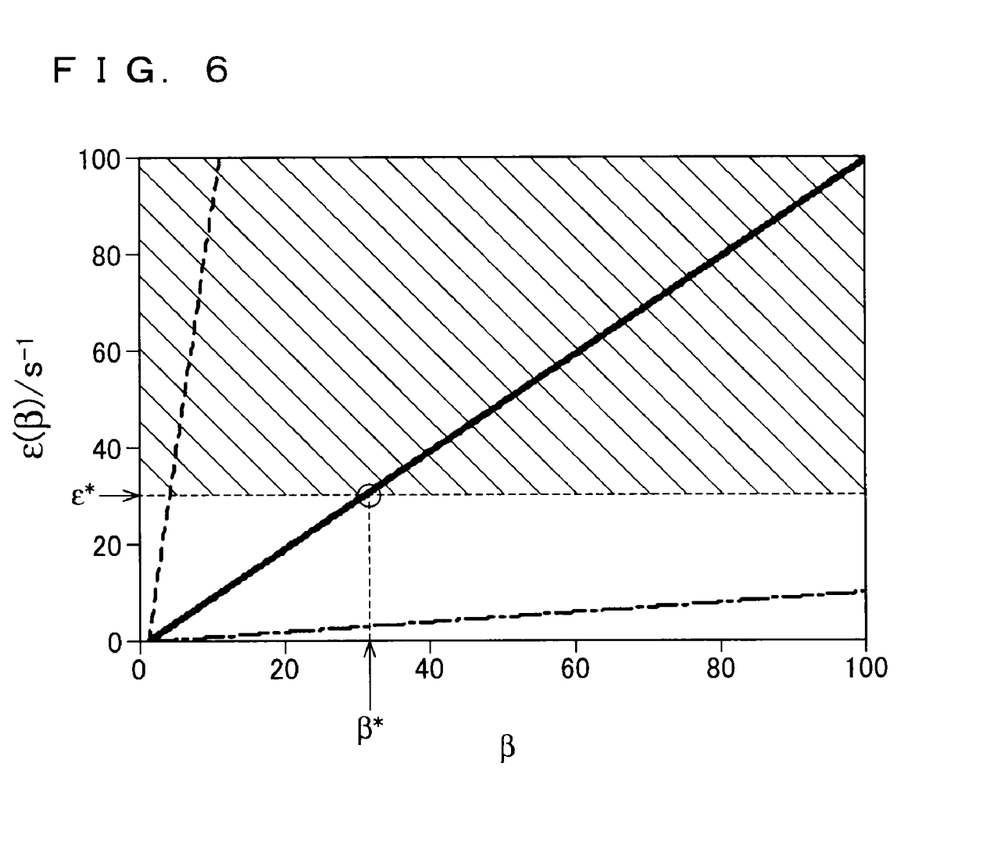
FIG. 6 is a graph showing a plot (one example) of a compression ratio $\beta$ against an elongation strain ration $\epsilon(\beta)$.

FIG. 6 illustrates a relationship (one example) between the elongation strain rate $\epsilon$ and a compression ratio $\beta$ obtained from Equation (5). From this, it can be understood that the oriented melt can be obtained by setting such that the time $\Delta t$ required for compression deformation is 1 second or less, if the critical elongation strain rate $\epsilon^*$ is 30 s$^{-1}$, and a die for giving a compression ratio $\beta$ of about 30.

(1-3: Step of Performing Crystallization by Rapid Cooling)

A step of performing crystallization by rapid cooling is described below, which is included in the method according to the present invention for producing the bulk polymer oriented crystals. The step of performing crystallization by rapid cooling is a step of cooling the polymer melt with the oriented melt state of the polymer melt maintained. The step of performing crystallization by rapid cooling causes the molecular chains in the polymer oriented melt to meet each other, thereby causing the nucleation and crystal growth without help of heterogeneity. In this way, the polymer oriented crystals are prepared.

If the polymer melt in the oriented melt state is allow to stand, the entropy is increase according to the thermodynamic law. As a result, the polymer melt is returned to the isotropic melt. Thus, to crystallize the polymer melt with the oriented melt state maintained, it is preferable to cool the polymer melt as fast as possible. Moreover, the environmental temperature (that is, "degree of supercooling $\Delta T$") at cooling the polymer melt is not particularly limited, provided that the temperature is lower than a melting temperature of the polymer. Especially, an optimal degree of supercooling significantly differs depending on the type of the polymer. Thus, the optimal degree of supercooling may be adopted as appropriate. For example, $\Delta T$ is preferably in a range of 20 to 60° C. in the case of polypropylene. A degree of supercooling less than the preferable range would lead to significantly slow crystallization rate, thereby resulting in a low yield of the polymer oriented crystals. A degree of supercooling more than the preferable range would lead to slow diffusion of the molecular chains, thereby resulting in a low crystallization rate.

Figure 7A:
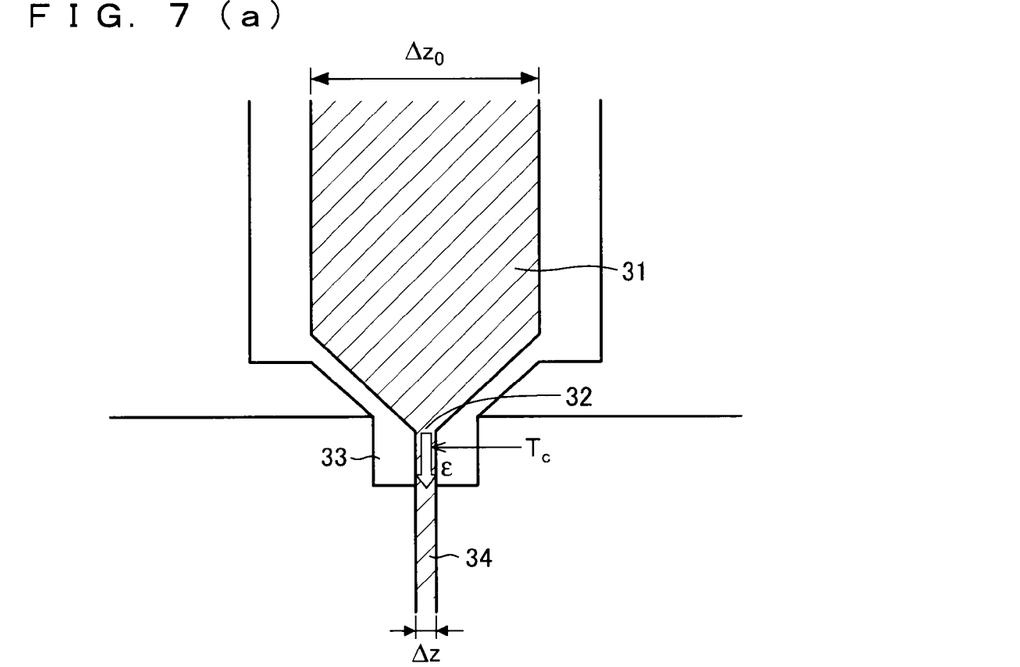
FIG. 7(a) is a schematic view of an apparatus (one example) for use in producing the polymer oriented crystals according to the present invention.

Moreover, the cooling may be carried out in a vapor phase or liquid phase. The cooling may be carried out by a method or means generally adopted in producing the polymer, or a modification thereof, as appropriate. FIG. 7(a) schematically illustrates an apparatus (one example) for use in the method according to the present invention for producing the polymer oriented crystals. This step is more specifically explained referring to this schematic view. For example, a polymer oriented melt 31 injected or extruded from a pore 32 of a die is brought to contact with a rapid cooling crystallization section 33 having a prescribed cooling temperature. With this, the polymer oriented crystals 34 are obtained in the downstream of the rapid cooling crystallization section 33. Moreover, the polymer oriented melt 31 extruded via the pore 32 may be cooled by passing the extruded polymer oriented melt 31 though a liquid (such as water) of the prescribed temperature. Moreover, the polymer oriented melt 31 extruded via the pore 32 may be cooled by exposing the extruded polymer oriented melt 31 to an environment of the prescribed cooling temperature. Moreover, the polymer oriented melt 31 extruded via the pore 32 may be cooled by bringing the extruded polymer oriented melt 31 to contact with a roller cooled to the prescribed cooling temperature. Furthermore, in case where the polymer oriented melt 31 is extruded into a mold via the die 33, the mold may be cooled to the prescribed cooling temperature.

Figure 7B:
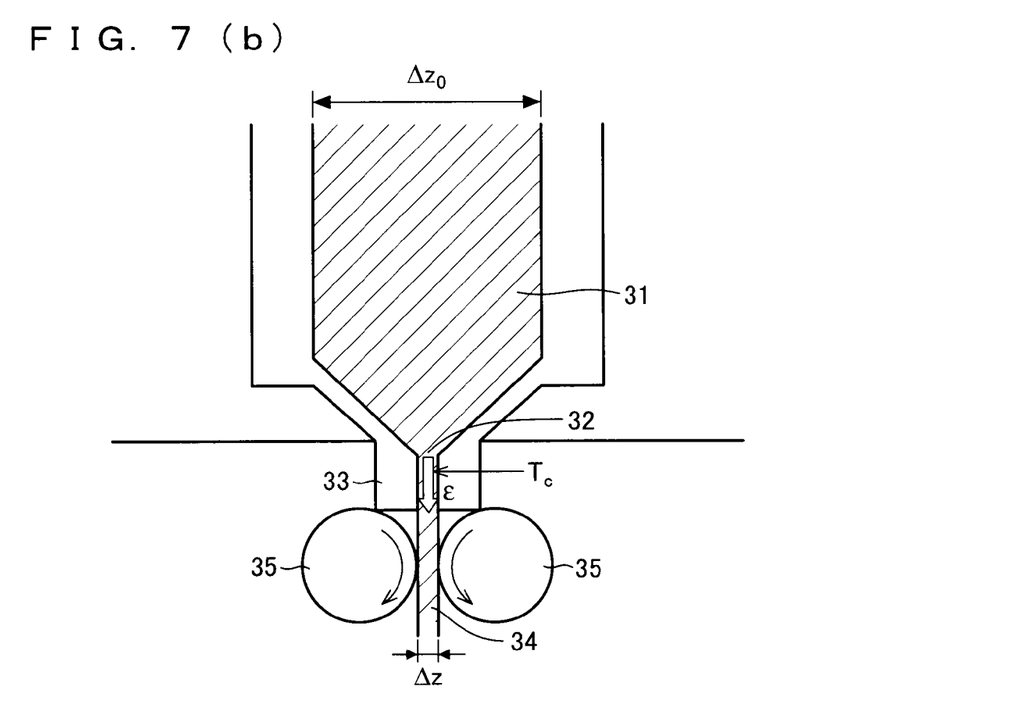
FIG. 7(b) is a schematic view of an apparatus (another example) for use in producing the polymer oriented crystals according to the present invention.

FIG. 7(b) illustrates another example of the apparatus for use in the method according to the present invention for producing the polymer oriented crystals. The apparatus as illustrated in FIG. 7(b) is an apparatus as illustrated in FIG. 7(a) with rollers 35 for pulling out the polymer oriented melt 31. The rollers 35 may be used for cooling the polymer oriented melt 31 to the prescribed cooling temperature.

<2. Polymer Oriented Crystals According to the Present Invention>

The polymer oriented crystals according to the present invention is produced by the method according to the present invention for producing the same. Thus, the polymer oriented crystals according to the present invention are bulk polymer oriented crystals, which have not been obtained conventionally. The bulk polymer oriented crystals according to the present invention are almost entirely made of close-packed shish, and are distinguishable from the conventional oriented crystal material "incomplete oriented crystal material including sparsely-existing shish and kebab that is a laminated lamellar structure surrounding shish", or a crystal that is very partially oriented like the "spiralite" discovered by the present inventions.

Possible applications of the polymer oriented crystals of the present invention encompass the followings, for example. The polymer oriented crystals of PP can be applied to most (90% or more) of interior parts of automobiles. Moreover, the polymer oriented crystals of PP are applicable to interior and exterior parts of conveyance machines such as automobiles, air plans, rockets, trains, ships, motorbikes, and bicycles, and parts or machine parts of machine tools, in replacement of metals. High rigidity and light weight of the polymer oriented crystals of PP make it possible to use it as diaphragm for speaker or microphone. Moreover, because it has a high transparency, the polymer oriented crystals of PP are applicable to CD and DVD in replacement of PC. Moreover, the high transparency thereof allows to use the polymer oriented crystals of PP as masks for liquid crystal/plasma displays. Moreover, with the high transparency, the polymer oriented crystals of PP can be used for medical tools or apparatus such as disposable syringe, tools for intravenous drips, drug containers, etc. Moreover, the highly transparent polymer oriented crystals of PP are applicable to various bottles, glass, small aquarium tank for home use, large aquarium tank for business use, in replacement of glass. Moreover, the highly transparent polymer oriented crystals of PP are applicable to contact lens, glass lens, and various optical lens. Moreover, the highly transparent polymer oriented crystals of PP are applicable to glass for buildings and houses. Further, with the high rigidity, high toughness, and light weight, the polymer oriented crystals of PP can be applied to various sports goods such as ski shoes, ski boards, boards, rackets, various nets, tents, knapsacks, and the like. Moreover, the high rigidity, high toughness, and light weight thereof makes it possible to use the polymer oriented crystals of PP in handcraft tools and decorating tools such as needles, scissors, sewing machines, etc. Furthermore, the polymer oriented crystals of PP are applicable to retailing products such as show windows and store display products. Moreover, the polymer oriented crystals of PP can be used in tools or facilities in parks, amusement parks, theme parks, such as joggling boards, see-saws, roller coasters, etc. Apart from these, the polymer oriented crystals of PP are applicable to: structuring materials constituting parts of electric, electronic, information apparatus or precision instruments such as clocks or box materials thereof; stationeries such as files, folders, pen cases, writing tools, scissors, etc.: cooking tools such as knifes, bowls, etc.; wrapping materials for foods, sweets, and tobaccos; food containers, tableware, disposable chopsticks, toothpicks; furniture such as home-use furniture, office furniture, etc.; building materials, interior materials, and exterior materials for building and houses; materials for roads or bridges; materials for toys; super tensile spike fibers and strings; fishery tools, fishing nets, and fishing tools; agricultural tools, agricultural goods, shopping bags, garbage bags; various pipes; gardening supplies; and transport containers, pallets, boxes; and the like.

Meanwhile, the polymer oriented crystals of PE are applicable to super tensile spike fibers and strings.

Meanwhile, the polymer oriented crystals of fluorine polymer such as polyvinylidene fluoride have a high ferroelectricity and piezoelectricity, which enables it to be applied to highly accurate supersonic elements, fast switching elements, high performance speaker, highly sensitive microphones, and the like.

Meanwhile, the polymer oriented crystals of PET are applicable to industrial materials required to have high heat tolerance against about 200° C.

EXAMPLE

In the following, the present invention is described more specifically referring to Example. It should be noted that the present invention is not limited these Examples.

[Method]

Isotactic polypropylene (referred to as "PP" in the present Example) used in elongation crystallization was prepared by the inventors of the present invention and had $M_w=30 \times 10^4$, $M_w/M_n=7$ (equilibrium melting temperature $T_m^0=187.3°$ C.), where $M_w$ is weight average molecular weight and $M_n$ is number average molecular weight. It was assumed that $T_m^0$ for $M_w$ was identical with $T_m^0$ of $M_w$ determined in K. Yamada, M. Hikosaka et al, J. Mac. Sci. Part B-Physics, B42(3&4), 733 (2003).

The PP thus prepared was shaped in a disc shape and placed on a lower transparent board 2 of a Compression-type crystallization apparatus 10 (hereinafter, crystallization apparatus). Then, an upper transparent board 1 was placed on top of the disc-shaped PP. The PP under this condition was melted at a temperature of 200.0° C., to prepare a PP melt. The PP melt was then cooled down at a cooling rate of 30° C./min to a crystallization temperature $T_c=148.0$ to 154.0° C. (degree of supercooling $\Delta T=33.3$ to 39.3K). Then, the sample (PP melt) was pressured at v=3 mm/sec. After that, elongation crystallization at a constant temperature ("isothermal elongation crystallization") was observed via a polarization microscope, thereby to measure a waiting time (τ) to required to generate crystallization. Put as a melting temperature $T_m$ is a temperature at which gradual melting occurred while the sample subjected to further elongation crystallization was kept at the constant temperature for 10 minutes or longer.

[Result]

I. Generation of Polymer Oriented Crystals and Critical Elongation Strain Rate $\epsilon^*$ After a certain waiting time τ, a bulk polymer crystal made of significantly fine and close-packed shish occurred at once in a region on or out of radius x of 7.0 mm of the disc-shaped sample (x≦7.0 mm) (see FIG. 8). The shish was so fine and close-packed beyond resolution power of the microscope. The creation of such significantly-close-packed shish without adding a nucleating agent in the present Example explained that "homogeneous nucleation" occurred in the polymer oriented crystals. It has been believed that the homogeneous nucleation can be observed only in droplet melts. Remarkably, it was first time in the world that the homogeneous nucleation was observed in crystallization of bulk polymer melt. In a region inside radius of 7.0 mm (x<7.0 mm), spherulite appeared after a well-long time elapsed from time τ. This showed that a critical elongation strain rate $\epsilon^*$ was present at x=7.0 mm (critical point radius x*). After the crystallization was completed, it was found that the bulk polymer oriented crystals portion were significantly high in transparency.

II. Critical Elongation Strain Rate $\epsilon^*(X^*)$

FIG. 2 illustrates curves obtained by plotting the elongation strain rates $\epsilon(x)$ against radius x of the disc-shaped sample. In FIG. 2, the solid curve shows the results of the present Example. The broken curve shows results obtained with v greater than that of the present Example. The dashed curve shows results obtained with v less than that of the present Example.

From FIG. 2, it was found that the elongation strain rate $\epsilon^*$ was 30 sec$^{-1}$ when the critical point radius x*=7.0 mm. This demonstrates that the elongation strain rate $\epsilon^*(x^*)$ of the PP melt was 30 sec$^{-1}$.

III. Melting Temperatures of Polymer Oriented Crystals and Spherulite

Figure 9:
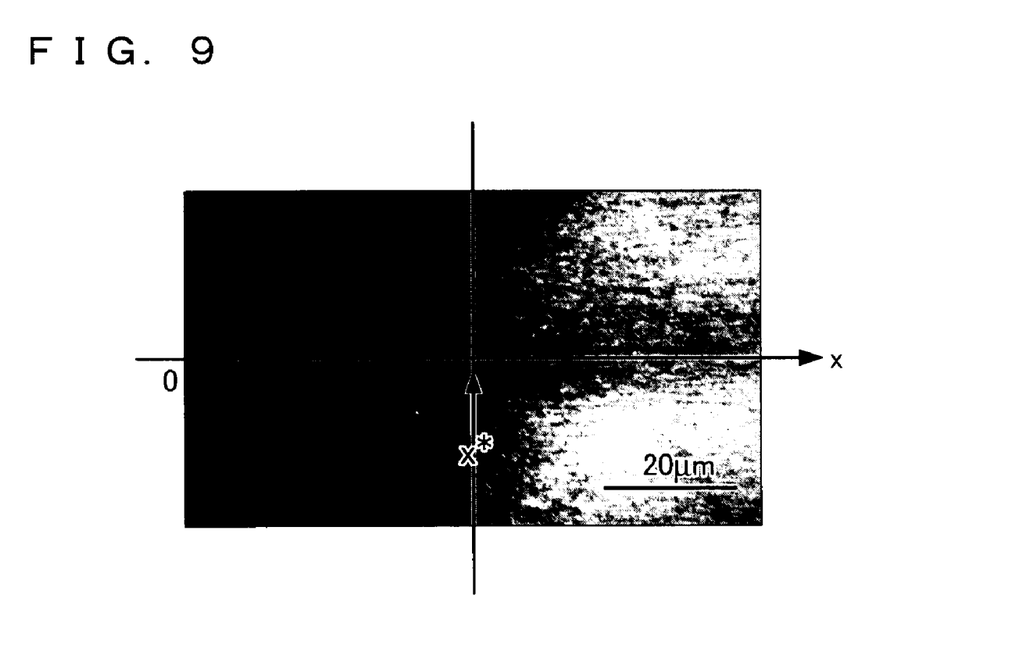
FIG. 9 is a microscopic view of a sample prepared by treating the sample of FIG. 8 at a constant temperature of 181.8° C. for 10 min.

The crystallized sample illustrated in FIG. 8 was kept at 181.8° C. (constant) for 10 min or longer, and observed via a polarization microscope. A polarization microscopic image is illustrated in FIG. 9. In FIG. 9, the gray portion is where the sample was not melted. The black portion is where the sample was melted. FIG. 9 demonstrates that the melting temperature in the region of x≦7.0 mm of the disc-shaped sample (i.e., the region where the polymer oriented crystals) was higher than that melting temperature in the region of spherulite.

The melting temperatures of the polymer oriented crystals and the spherulite were measured: they were 183.3° C. and 175.0° C., respectively. The melting temperature of the polymer oriented crystals was close to $T_m^0$=187.3° C. (it was lower than $T_m^0$ by just 4° C.), and higher than widely known melting temperatures (approximately 170° C.) of general PP spherulites by ten and several degrees. The melting temperature of the polymer oriented crystals was higher than the melting temperature of the spherulites by 8.3° C. This suggested that the polymer oriented crystals were Elongated Chain Crystal (ECC). No ECC of PP has been reported so far.

Figure 10:
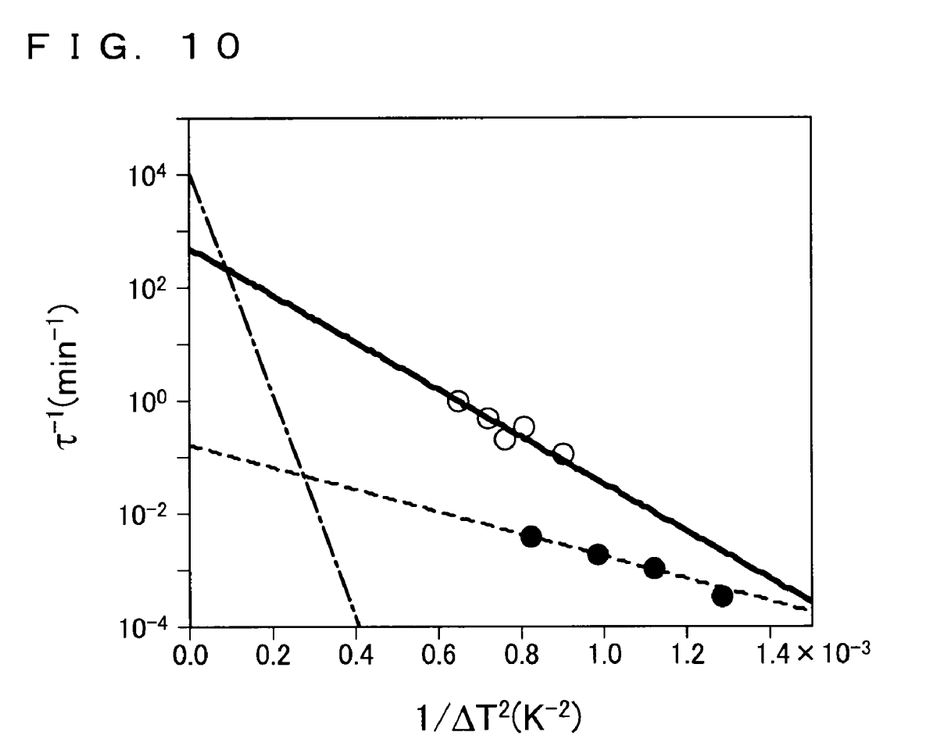
FIG. 10 is a graph plotting $\tau^{-1}$ against $\Delta T^{-2}$ in oriented crystal and spherulite prepared by elongation crystallization of isotactic polypropylene melt in an Example.

FIG. 10 is a graph plotting "an inverse number $\tau^{-1}$ of the waiting time v required to occur the crystallization" against $\Delta T^{-2}$. In FIG. 10, the solid line shows the results of the polymer oriented crystals. The broken line shows the results of general spherulite. Here, ΔT is degree of supercooling.

From the graph in FIG. 10, the following empirical formula was obtained:

$$\tau^{-1} \propto \exp(-C/\Delta T^2) \quad (6),$$

where C is a constant.

Moreover, $\tau^{-1}$ was equal to $\tau_c^{-1}$ in the equation $\tau_c^{-1}$=exp$(-\Delta G^*/kT)$=exp$(-C/\Delta T^2)$ . . . (7) of critical nucleation based on the well-known nucleation theory (see H. L. Frisch and C. C. Carlier, J. Chem. Phys. 10, 4326-4330, 1971). Here, $\Delta G^*$ is free energy of critical nucleation and satisfies $C \propto \Delta G^*$ . . . (8). Thus, $\Delta G^*$ corresponds to the gradient of the line. Here, the "critical nucleus" is an activated state that is rate-determining process in the nucleation process.

FIG. 10 also shows a plot (indicated by dashed line) of $\tau^{-1}$ against $\Delta T^{-2}$ in the homogeneous nucleation in the spherulite. In the homogeneous nucleation, $C \propto \sigma^2 \sigma_e$, thus, it was satisfied that $(\sigma^2\sigma_e)^{Shish}$=2.6×10$^{-7}$ (J$^3$/m$^6$)<<$(\sigma^2\sigma_e)^{Sph}$=11.3× 10$^{-7}$ (J$^3$/m$^6$) . . . (10). Here, σ and $\sigma_e$ are surface free energy on a side surface and on an end surface, respectively. The superscripts "shish" and "sph" indicate shish and spherulite, respectively. It was found that $\Delta G^{*Shish} \ll \Delta G^{*sph}$.

It can be theoretically predicted that σ and $\sigma_e$ are significantly small in the oriented melt (for example, see Non-Patent Citations 2 and 3). Thus, can be predicted that $\Delta G^*$ is significantly small. Therefore, it was showed from the above result that the "oriented melt" was obtained at strain rate equal to or greater than the critical elongation strain rate".

VI. Conclusion

The above-described kinetics study demonstrates that elongation crystallization at strain rate greater than or equal to at critical elongation strain rate results in oriented melt and consequently polymer oriented crystals (Shish).

V. Tensile Strength of Polymer Oriented Crystals

Tensile strength of the polymer oriented crystals thus produced was measured. More specifically, a sample (2 mm×5 mm×0.1 mm) of the polymer oriented crystals was set in a tensile strength measuring apparatus, which the inventors of the present invention designed and created for testing small sample. The tensile strength was measured by pulling the sample at a rate at which the sample was torn in 10 to 30 seconds after the start of the pulling.

The result is shown on Table 1, where tensile strengths of the followings are also given for comparison: PE, PP (not elongated) (data of PE and not-elongated PP are from "Polypropylene Handbook, E. P. Moor, Kogyo Chosakai Publishing, Inc., 1998, P 295), PET (Ikuo, NARISAWA, Mechanical Properties of Plastics, Sigma Publishing Co., Ltd., 1994, P 90), metals (Aluminum (Al), brass, stainless steel, steel (SNCM7)). The data of the metals are quoted from (Iida, et al., Table of Physical Properties of Materials, Asakura Publishing Co., Ltd., 1969, P 187-191).

TABLE 1

|  | Tensile Strength (GPa) |
|---|---|
| Polymer Oriented Crystals (PP) | 0.1-0.15 |
| PE | 0.03-0.07 |
| PP (not elongated) | 0.04-0.06 |
| PET | 0.06 |

TABLE 1-continued

|  | Tensile Strength (GPa) |
|---|---|
| Al | 0.1 |
| Brass | 0.4 |
| Stainless Steel | 0.5 |
| Steel (SNCM7) | 1 |

The results in Table 1 shows that the tensile strength of the polymer oriented crystals (PP) was significantly higher than these of the commercially-available PP (not elongated) and PE, and equivalent to or greater than these of PET and Al.

This confirmed that the application of the present invention to PP makes it possible to replace the engineering plastics or metals with PP, which is a general-purpose plastic.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, the present invention makes it possible to produce polymer oriented crystals. This allows to use a general-purpose plastic to replace the engineering plastic. Thereby, the present invention can make remarkable reduction in the cost of various industrial products made of polymers. Furthermore, the present invention can give a polymer a strength equivalent to these of metals, and allows to use the polymer in replacement of the metals.

Therefore, the present invention is applicable to not only various industries using polymer parts but also industries using metal parts.

The invention claimed is:

1. A method for producing polymer oriented crystals, the method comprising:
preparing an oriented melt by subjecting a polymer melt to elongation at a strain rate equal to or greater than a critical elongation strain rate so as to put the polymer melt in an oriented melt state; and
rapidly cooling the polymer oriented melt, which is obtained in the step of preparing it, to crystallize it while keeping the oriented melt state,
the critical elongation strain rate being:
(I) a critical elongation strain rate $\epsilon^*$ determined by:
sandwiching the polymer melt with transparent boards, the polymer melt having a disc shape with a radius of $x_0$ and a thickness of $\Delta z_0$;
supercooling the polymer melt;
pressing the polymer melt at a constant value v in a thickness direction by using the transparent boards;
measuring a critical point radius $x^*$ at which oriented crystals are formed from the polymer melt; and
calculating the critical elongation strain rate $\epsilon^*$ from:
$\epsilon^* = \alpha x^{*3}$,
where $\alpha = v/(2 x_0^3 \Delta z_0)$; or
(II) a critical elongation strain rate $\epsilon^*$ determined by:
sandwiching the polymer melt with transparent boards, the polymer melt having a rectangular shape with a center distance of $x'_0$, a thickness of $\Delta z_0$, and a constant width;
supercooling the polymer melt;
pressing the polymer melt at a constant rate v in a thickness direction by using the transparent boards;
measuring a critical point center distance $x'^*$ at which oriented crystal are formed from the polymer melt; and
calculating the critical elongation strain rate $\epsilon^*$ from:
$\epsilon^* = \alpha x'^{*2}$,
where $\alpha = v/(2 x'^2_0 \Delta z_0)$.

2. The method as set forth in claim 1, further comprising:
determining the critical elongation strain rate of the polymer melt.

3. The method as set forth in claim 1, wherein the polymer melt is a polypropylene melt.

4. The method as set forth in claim 1, wherein the polymer melt is an isotactic polypropylene melt.

5. Polymer oriented crystals produced by the method as set forth in claim 1, the polymer oriented crystals having a solid content which contains highly oriented molecular chains by 50% or more.

6. A method for producing polymer oriented crystals, the method comprising:
determining a critical elongation strain rate of a polymer melt;
preparing an oriented melt by subjecting the polymer melt to elongation at strain rate equal to or greater than a critical elongation strain rate, which is obtained in the step of determining, so as to put the polymer melt in an oriented melt state; and
rapidly cooling the polymer oriented melt, which is obtained in the step of preparing it, to crystallize it while keeping the oriented melt state
wherein the step of determining the critical elongation strain rate of the polymer melt comprises:
sandwiching the polymer melt with transparent boards, the polymer melt having a disc shape with a radius of $x_0$ and a thickness of $\Delta z_0$;
supercooling the polymer melt;
pressing the polymer melt at a constant rate v in a thickness direction by using the transparent boards;
measuring a critical point radius $x^*$ at which oriented crystals are formed from the polymer melt; and
calculating the critical elongation strain rate from:
$\epsilon^* = \alpha x^{*3}$,
where $\alpha = v/(2 x_0^3 \Delta z_0)$.

7. A method for producing polymer oriented crystals, the method comprising:
determining a critical elongation strain rate of a polymer melt;
preparing an oriented melt by subjecting the polymer melt to elongation at strain rate equal to or greater than a critical elongation strain rate, which is obtained in the step of determining, so as to put the polymer melt in an oriented melt state; and
rapidly cooling the polymer oriented melt, which is obtained in the step of preparing it, to crystallize it while keeping the oriented melt state
wherein the step of determining the critical elongation strain rate of the polymer melt comprises:
sandwiching the polymer melt with transparent boards, the polymer melt having a rectangular shape with a center distance of $x'_0$, a thickness of $\Delta z_0$, and a constant width;
supercooling the polymer melt;
pressing the polymer melt at a constant rate v in a thickness direction by using the transparent boards;
measuring a critical point center distance $x'^*$ at which oriented crystals are formed from the polymer melt; and
calculating the critical elongation strain rate from:
$\epsilon^* = \alpha x'^{*2}$,
where $\alpha = v/(2x'^2_0 \Delta z_0)$.

8. A method for determining a critical elongation strain rate of a polymer melt, the method comprising:

sandwiching the polymer melt with transparent boards, the polymer melt having a disc shape with a radius of $x_0$ and a thickness of $\Delta z_0$;

supercooling the polymer melt;

pressing the polymer melt at a constant rate v in a thickness direction by using the transparent boards;

measuring a critical point radius $x^*$ at which oriented crystals are formed from the polymer melt; and calculating the critical elongation strain rate $\epsilon^*$ from:

$\epsilon^* = \alpha x^{*3}$, where $\alpha = v/(2x_0^3 \Delta z_0)$.

9. A method for determining a critical elongation strain rate of a polymer melt, the method comprising:

sandwiching the polymer melt with transparent boards, the polymer melt having a rectangular shape with a center distance of $x'_0$, a thickness of $\Delta z_0$, and a constant width;

supercooling the polymer melt;

pressing the polymer melt at a constant rate v in a thickness direction by using the transparent boards;

measuring a critical point center distance $x'^*$ at which oriented crystals are formed from the polymer melt; and calculating the critical elongation strain rate $\epsilon^*$ from:

$\epsilon^* = \alpha x'^{*2}$, where $\alpha = v/(2{x'_0}^2 \Delta z_0)$.

\* \* \* \* \*